United States Patent
Cawley et al.

[11] Patent Number: 5,807,294
[45] Date of Patent: Sep. 15, 1998

[54] ADJUSTABLE HINGE ASSEMBLY FOR AN OSTEOARTHRITIC KNEE BRACE

[75] Inventors: Patrick W. Cawley, Carlsbad; Jeffrey T. Mason, Escondido, both of Calif.

[73] Assignee: Breg, Inc., Vista, Calif.

[21] Appl. No.: 820,876

[22] Filed: Mar. 21, 1997

[51] Int. Cl.⁶ .................................................... A61F 5/32
[52] U.S. Cl. ................. 602/26; 602/16; 602/25; 602/32; 128/103.1; 128/106.1
[58] Field of Search ............................... 602/5, 6, 12, 16, 602/23, 25, 26, 27, 32, 35, 36, 38; 128/103.1, 105.1, 107.1, 106.1, 108.1, 109.1, 110.1, 121.1, 882

[56] References Cited

U.S. PATENT DOCUMENTS

| Re. 34,818 | 1/1995 | Daneman et al. . | |
|---|---|---|---|
| 3,669,105 | 6/1972 | Castiglia . | |
| 4,372,298 | 2/1983 | Lerman | 602/26 |
| 4,428,369 | 1/1984 | Peckham et al. . | |
| 4,602,627 | 7/1986 | Vito et al. . | |
| 4,697,583 | 10/1987 | Mason et al. | 602/16 |
| 4,796,610 | 1/1989 | Cromartie . | |
| 4,803,975 | 2/1989 | Meyers . | |
| 4,940,045 | 7/1990 | Cromartie . | |
| 5,042,464 | 8/1991 | Skwor et al. . | |
| 5,063,917 | 11/1991 | Young et al. . | |
| 5,086,760 | 2/1992 | Neumann et al. . | |
| 5,277,698 | 1/1994 | Taylor . | |
| 5,316,547 | 5/1994 | Gildersleeve . | |
| 5,458,565 | 10/1995 | Tillinghast, III et al. . | |
| 5,520,622 | 5/1996 | Bastyr et al. . | |
| 5,527,268 | 6/1996 | Gildersleeve et al. . | |
| 5,542,911 | 8/1996 | Cassford et al. . | |
| 5,586,970 | 12/1996 | Morris et al. . | |

FOREIGN PATENT DOCUMENTS 518676   2/1931   Germany ................................. 602/23

*Primary Examiner*—Richard J. Apley
*Assistant Examiner*—Victor K. Hwang
*Attorney, Agent, or Firm*—Rodney F. Brown

[57] ABSTRACT

A hinge assembly is provided for an orthopedic knee brace that pivotally couples a first rotation member and a second rotation member. The hinge assembly includes a pad assembly, a hinge, and first and second adjustment members enabling adjustment of the normal force applied by the hinge assembly to the knee joint for the effective treatment of osteoarthritis. The hinge includes an end of the first rotation member, an end of the second rotation member, first and second hinge plates positioned on opposite sides of the ends, and first and second hinge fasteners. The first and second hinge fasteners each has a bore therethrough that is internally threaded. The first hinge fastener rotatably connects the end of the first rotation member to the first and second hinge plates and the second hinge fastener rotatably connects the end of the second rotation member to the first and second hinge plates. The first adjustment member has external threads that are received by the internal threads of the first hinge fastener to telescopically couple the first adjustment member to the first hinge fastener. The second adjustment member likewise has external threads that are received by the internal threads of the second hinge fastener to telescopically couple the second adjustment member to the second hinge fastener. Both the first and second adjustment members have ends that are substantially fixedly coupled to the pad holder. As a result selective displacement of the pad assembly toward or away from the hinge is enabled when the user selectively displaces the first and second adjustment members through the first and second bores of the first and second hinge fasteners.

19 Claims, 6 Drawing Sheets

# ADJUSTABLE HINGE ASSEMBLY FOR AN OSTEOARTHRITIC KNEE BRACE

TECHNICAL FIELD

The present invention relates generally to orthopedic braces, particularly to an brace for an osteoarthritic knee joint, and more particularly to an adjustable hinge assembly for an osteoarthritic knee brace.

BACKGROUND OF THE INVENTION

Orthopedic knee braces are worn on the leg of a user either to support a healthy knee joint that is at risk of injury or to stabilize a knee joint that has been destabilized by an injury or other condition. Orthopedic knee braces generally include rigid structural components to support or stabilize the knee joint. Typically, the rigid structural components are dynamically linked together by one or more hinges enabling controlled pivotal movement of the knee joint during user activity or rehabilitative therapy. The brace is positioned on the leg such that the hinges traverse the knee joint, while the rigid components are secured to the leg at a plurality of engagement faces above and below the knee joint.

One destabilizing condition of the knee joint is osteoarthritis, a degenerative disease that results in chronic pain to the subject when the knee joint is statically or dynamically loaded. Osteoarthritis is commonly the result of aging, knee joint overuse, or injury. Osteoarthritic pain is caused by an unbalanced loading on the medial or lateral compartment of the knee joint which closes the clearance space forming the compartment between the condyles of the femur and tibia. When there is contact of the condyles in the afflicted compartment of the knee joint, abrasion occurs at the contact surface producing pain in the joint. Wearing an orthopedic knee brace on the affected leg is a common noninvasive means of treating osteoarthritis to reduce the osteoarthritic pain associated therewith. A number of orthopedic knee braces are designed specifically to treat osteoarthritis by applying a corrective force to the leg of the user proximal to the knee joint, such as the knee brace disclosed in U.S. Pat. No. 5,277,698. Nevertheless, the present invention recognizes the orthopedic knee brace that treats osteoarthritis more effectively than those braces known in the prior art.

Accordingly, it is an object of the present invention to provide an orthopedic knee brace for effective treatment of osteoarthritis in the knee joint. More particularly, it is an object of the present invention to provide a hinge assembly for an orthopedic knee brace that effectively treats osteoarthritis in the knee joint and relieves the user of knee joint pain. It is a further object of the present invention to provide a hinge assembly for an osteoarthritic knee brace that applies an effective treatment force to the knee joint of the user. It is yet another object of the present invention to provide a hinge assembly for an osteoarthritic knee brace, wherein the treatment force applied by the hinge assembly to the knee joint is readily adjustable to the specific requirements of the user. These objects and others are achieved by the invention described hereafter.

SUMMARY OF THE INVENTION

The present invention is a hinge assembly for an orthopedic knee brace that pivotally couples a first rotation member and a second rotation member of the brace. The hinge assembly comprises a pad assembly, a hinge, and first and second adjustment members that enable selective displacement of the pad assembly toward or away from the hinge and consequently enable adjustment of the normal lateral or medial treatment force applied by the hinge assembly to the knee joint for the effective treatment of osteoarthritis. The pad assembly is configured to receive the knee joint of the user and includes a pad holder formed from a relatively stiffened material and a pad formed from a cushioning material coupled to the pad holder.

The hinge includes an end of the first rotation member, an end of the second rotation member, and first and second hinge plates positioned on opposite sides of the ends of the first and second rotation members. The end of the first rotation member has a first rotation aperture extending therethrough and the end of the second rotation member has a second rotation aperture extending therethrough. Each hinge plate also has a first hinge aperture and a second hinge aperture extending therethrough. The first hinge apertures of the first and second hinge plates are aligned with the first rotation aperture to form a first continuous fastener opening through the hinge. The second hinge apertures of the first and second hinge plates are similarly aligned with the second rotation aperture to form a second continuous fastener opening through the hinge. The hinge further includes a first hinge fastener having a first bore therethrough with first internal threads and a second hinge fastener having a second bore therethrough with second internal threads. The first hinge fastener is received within the first continuous fastener opening to rotatably connect the end of the first rotation member to the first and second hinge plates. The second hinge fastener is received within the second continuous fastener opening to rotatably connect the end of the second rotation member to the first and second hinge plates.

The first adjustment member has first external threads that are received by the first internal threads within the first bore of the first hinge fastener to telescopically couple the first adjustment member to the first hinge fastener. The second adjustment member likewise has second external threads that are received by the second internal threads within the second bore of the second hinge fastener to telescopically couple the second adjustment member to the second hinge fastener. Both the first and second adjustment members have ends that are substantially fixedly coupled to the pad holder such that the linear position of the ends of the first and second adjustment members are fixed relative to the pad holder, although the ends of the first and second adjustment members are preferably free to rotate relative to the pad holder. As a result selective displacement of the pad assembly relative to the hinge is enabled when the user selectively displaces the first and second adjustment members through the first and second bores of the first and second hinge fasteners.

The invention will be further understood from the accompanying drawings and description.

DESCRIPTION OF PREFERRED EMBODIMENTS

Figure 1:
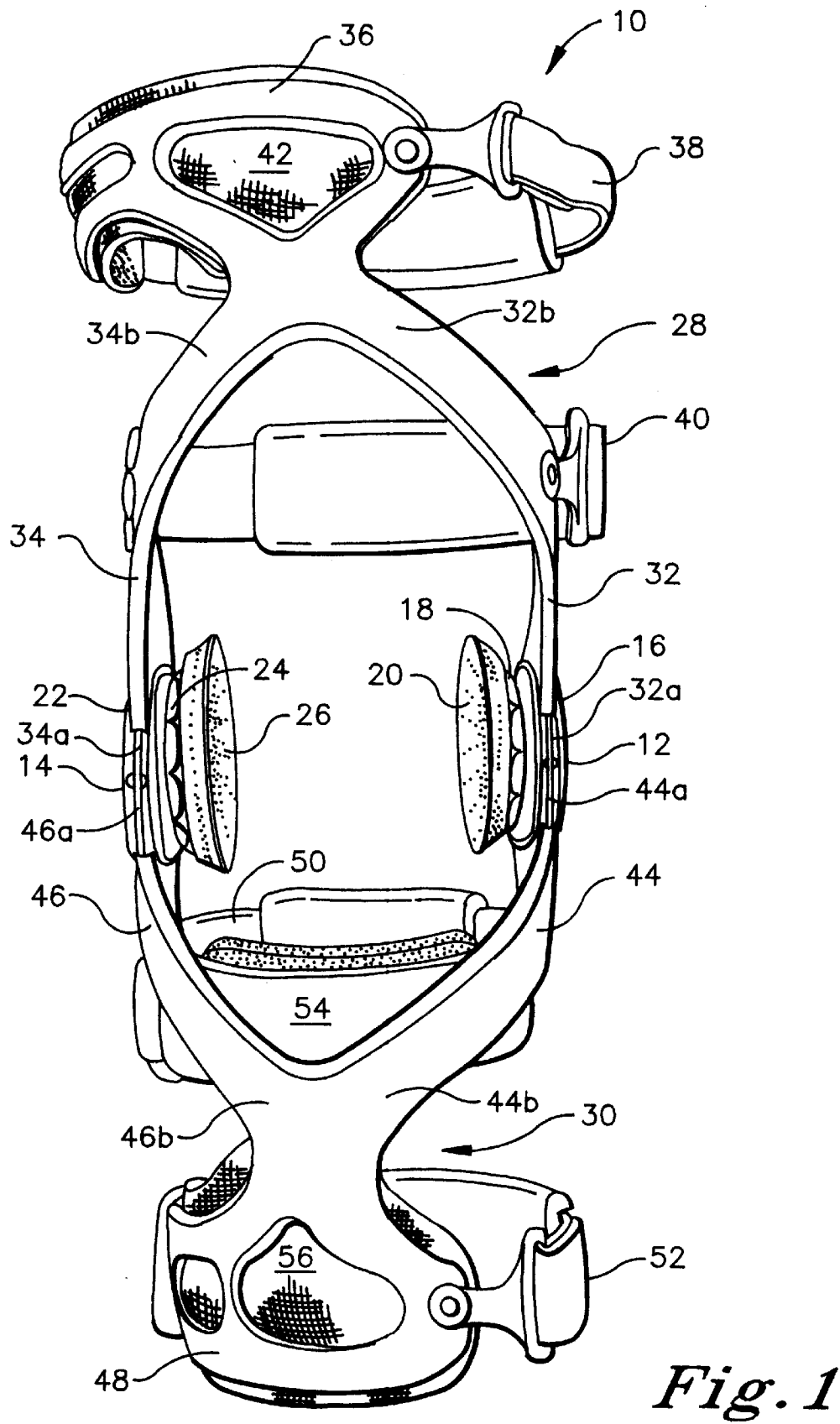
FIG. 1 is a perspective view of an orthopedic knee brace incorporating an adjustable hinge assembly of the present invention.

Referring initially to FIG. 1, an exemplary orthopedic knee brace incorporating the adjustable hinge assembly of the present invention is shown and generally designated 10. For purposes of illustration, the orthopedic knee brace 10 is configured for mounting on the right leg (not shown) of a human body. It is understood, however, that the skilled artisan can readily adapt the orthopedic knee brace 10 for mounting on the opposite leg in accordance with the instant teaching. The orthopedic knee brace 10 includes a medial hinge assembly 12 and a lateral hinge assembly 14. The medial hinge assembly 12 is provided with a medial hinge 16 and a medial pad assembly comprising a medial pad holder 18 and a medial pad 20. The lateral hinge assembly 14 is similarly provided with a lateral hinge 22 and a lateral pad assembly comprising a lateral pad holder 24 and a lateral pad 26. It is noted that the lateral hinge assembly 14 embodies the adjustable hinge assembly of the present invention as will be described hereafter.

The orthopedic knee brace 10 further comprises an upper brace assembly 28 and a lower brace assembly 30 opposingly positioned about the medial and lateral hinge assemblies 12, 14. The upper brace assembly 28 includes upper medial and lateral arms 32, 34 which are elongated rotation members. Each arm 32, 34 has a lower proximal end 32a, 34a rotatably coupled with the medial and lateral hinges 16, 22, respectively. The upper medial and lateral arms 32, 34 each also have an upper distal end 34b, 32b coupled with an upper anterior cuff 36. The upper brace assembly 28 extends substantially the length of the upper leg of the user and is retained in removable engagement with the upper leg by means of first and second upper adjustable straps 38, 40. An upper anterior pad 42 is provided to cushion the anterior of the user's upper leg from the upper anterior cuff 36 and secure the fit of the orthopedic knee brace 10 with the upper leg. The terms "proximal" and "distal" as used herein define the vertical position of an element relative to the knee joint. The terms "medial" and "lateral" and "anterior" and "posterior" define the horizontal position of an element relative to the longitudinal axis of the body.

The lower brace assembly 30 includes lower medial and lateral arms 44, 46, which are elongated rotation members. Each arm 44, 46 has an upper proximal end 44a, 46a rotatably coupled with the medial and lateral hinges 16, 22, respectively. The lower medial and lateral arms 44, 46 each also have a lower distal end 44b, 46b coupled with a lower anterior cuff 48. The lower brace assembly 30 extends substantially the length of the lower leg of the user and is retained in removable engagement with the lower leg by means of first and second lower adjustable straps 50, 52. First and second lower anterior pads 54, 56 are provided to cushion the anterior portion of the user's lower leg from the lower medial and lateral arms 44, 46 and from the lower anterior cuff 48, respectively, and to secure the fit of the orthopedic knee brace 10 with the lower leg.

Figure 2:
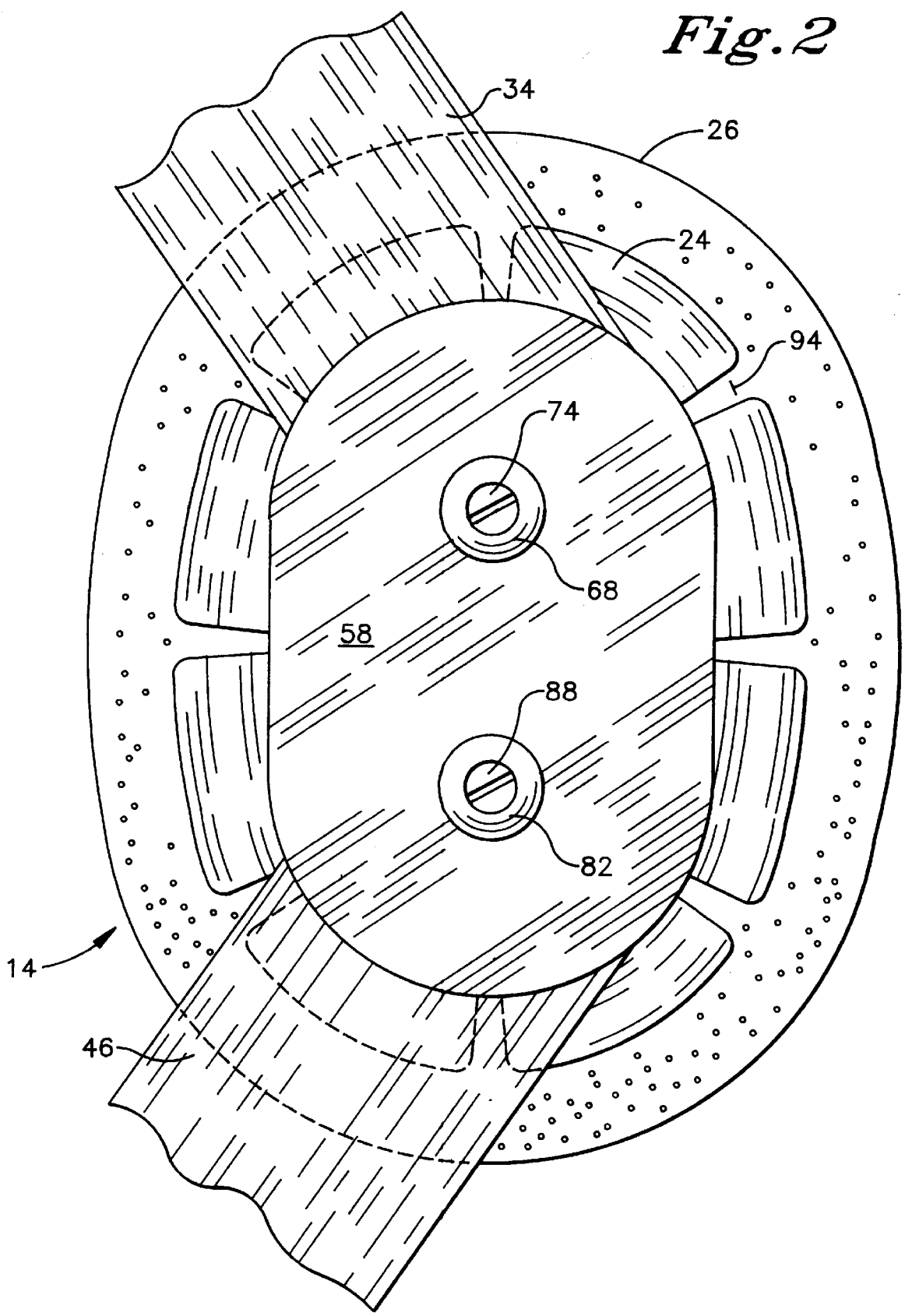
FIG. 2 is a frontal view of the adjustable hinge assembly of FIG. 1.
Figure 3:
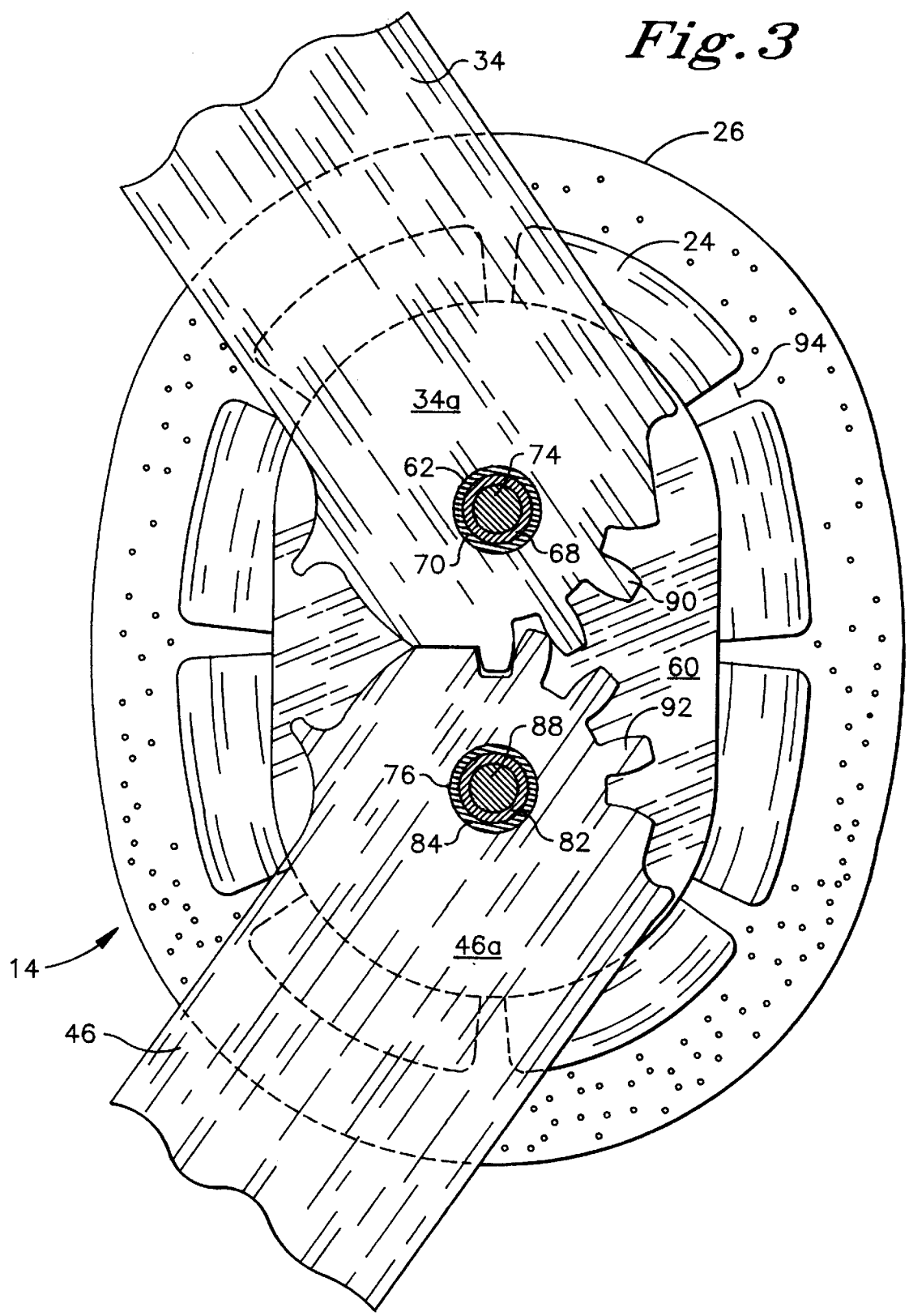
FIG. 3 is a frontal cut away view of the adjustable hinge assembly of FIG. 1.

Referring to FIGS. 2 and 3, the adjustable lateral hinge assembly 14 is illustrated in greater detail. The lateral hinge 22 comprises an outer hinge plate 58 and an inner hinge plate 60. The outer and inner hinge plates 58, 60 have a substantially identical construction, for example as described in U.S. patent application Ser. No. 08/656,088 filed on May 31, 1996, incorporated herein by reference. The lower proximal end 34a of the upper lateral arm 34 and the upper proximal end 46a of the lower lateral arm 46 are positioned between the outer and inner hinge plates 58, 60. The lower proximal end 34a has a rotation aperture 62 that aligns with a corresponding outer upper hinge aperture 64 and inner upper hinge aperture 66 (shown in FIGS. 4–6) formed in the outer and inner hinge plates 58, 60, respectively. Alignment of the apertures 62, 64, 66 enables rotatable attachment of the lower proximal end 34a to the outer and inner hinge plates 58, 60 by means of an upper hinge fastener 68, preferably a rivet, received by the apertures 62, 64, 66. An upper bushing 70 is also positioned within the apertures 62, 64, 66 between the lower proximal end 34a and the upper hinge fastener 68 to facilitate rotation of the upper lateral arm 34 about the lateral hinge 22 by reducing friction between the lower proximal end 34a and the upper hinge fastener 68. A female internally-threaded central bore 72 extends longitudinally through the upper hinge fastener 68 to receive a male externally-threaded upper adjustment member 74 that enables the user to adjust the position of the upper portion of the lateral pad holder 24 and lateral pad 26 relative to the lateral hinge 22 in a manner described hereafter.

The upper proximal end 46a similarly has a rotation aperture 76 that aligns with a corresponding outer lower hinge aperture 78 and inner lower hinge aperture 80 (shown in FIGS. 4–6) formed in the outer and inner hinge plates 58, 60, respectively. Alignment of the apertures 76, 78, 80 enables rotatable attachment of the upper proximal end 46a to the outer and inner hinge plates 58, 60 by means of a lower hinge fastener 82, preferably a rivet, received by the apertures 76, 78, 80. A lower bushing 84 is also positioned within the apertures 76, 78, 80 between the upper proximal end 46a and the lower hinge fastener 82 to facilitate rotation of the lower lateral arm 46 about the lateral hinge 22. A female internally-threaded central bore 86 extends longitudinally through the lower hinge fastener 82 to receive a male externally-threaded lower adjustment member 88 that enables the user to adjust the position of the lower portion of the lateral pad holder 24 and lateral pad 26 relative to the lateral hinge 22 in a manner described hereafter.

The lower proximal end 34a and the upper proximal end 46a are preferably provided with intermeshing teeth 90, 92, respectively, that maintain symmetric movement of the upper lateral arm 34 and the lower lateral arm 46 relative to the lateral hinge 22 in a conventional manner. Although not shown, it is also apparent to the skilled artisan that an operational hinge without the intermeshing teeth can be provided within the scope of the present invention. It is further within the purview of the skilled artisan to provide the lateral hinge 22 with stops, such as disclosed in U.S. patent application Ser. No. 08/656,088, that restrict the range of rotation of the upper and lower lateral arms 34, 46. It is also within the purview of the skilled artisan to provide additional means of securing the outer and inner hinge plates 58, 60 to one another, such as supplemental screws disclosed in U.S. patent application 08/656,088.

The lateral hinge assembly further comprises the lateral pad holder 24 and the lateral pad 26. The lateral pad holder 24 is a plate having a slightly concave shape. The lateral pad holder 24 is selectively positioned adjacent the inner hinge plate 60 and is attached to the lateral hinge 22 by means of the upper and lower adjustment members 74, 88 in a manner described hereafter. The lateral pad holder 24 is formed from a stiffened yet somewhat flexible material such as a conventional plastic. A plurality of flexion slits 94 are formed in the periphery of the lateral pad holder 24 to enhance the flexibility thereof.

The lateral pad 26 is a thickened continuous cushion formed from a conventional pliant padding material, such as a foam, or is alternatively a fluid-containing cushion, such as a pneumatic bladder. The lateral pad 26 is attached to the lateral pad holder 24, conforming to the shape thereof to receive the knee condyle of a user in substantial alignment with the normal axis of rotation of the knee joint. Attachment of the lateral pad 26 to the lateral pad holder 24 may be substantially permanent by conventional means such as glue or may be selectively detachable by conventional means such as a hook and loop fastener known by the tradename VELCRO.

Figure 4:
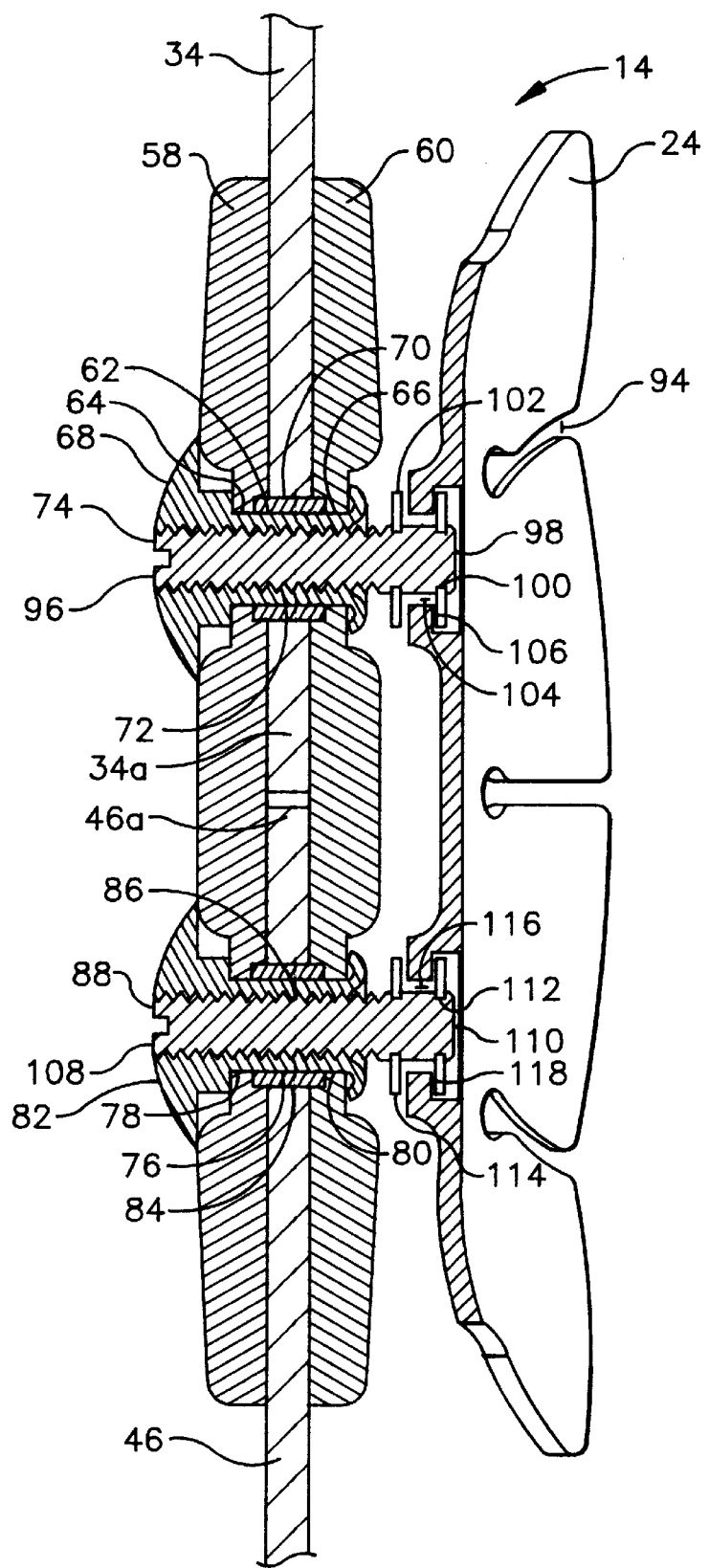
FIG. 4 is a cross-sectional view of the adjustable hinge assembly of FIG. 1 shown in a retracted position.

Adjustment of the lateral hinge assembly 14, and in particular adjustment of the position of the lateral pad holder 24 and lateral pad 26 relative to the position of the lateral hinge 22, is provided by the upper and lower adjustment members 74, 88, in cooperation with the upper and lower hinge fasteners 68, 82 and the lateral pad holder 24, as described in greater detail with reference to FIG. 4, wherein the lateral pad has been omitted from the lateral hinge assembly 14 for clarity. As described above, the apertures 62, 64, 66 are aligned to receive the upper hinge fastener 68 and the apertures 76, 78, 80 are aligned to receive the lower hinge fastener 82, thereby maintaining the relative positioning of the outer hinge plate 58, inner hinge plate 60, lower proximal end 34a, and upper proximal end 46a.

The upper adjustment member 74 is a conventional screw positioned in the central bore 72 of the upper hinge fastener 68 such that the external threads of the upper adjustment member 74 are telescopically coupled with the internal threads of the central bore 72. The head 96 of the upper adjustment member 74 is configured to receive an adjusting tool (not shown), such as a conventional screwdriver or Allen wrench. The opposite end 98 of the upper adjustment member 74 is configured with fastening slots 100 to receive an upper pad assembly fastener 102. The lateral pad holder 24 is provided with an upper opening 104 to receive the end 98 of the upper adjustment member 74 and about which the upper pad assembly fastener 102 is mounted, enabling fixed retention of the end 98 of the upper adjustment member 74 within the upper opening 104 of the lateral pad holder 24. The upper pad assembly fastener 102 can be substantially any fastening means that enables the upper adjustment member 74 to rotate freely relative to the upper fastener 102 and the lateral pad holder 24 without permitting substantial linear longitudinal movement of the upper adjustment member 74 within the upper opening 104. The present upper pad assembly fastener 102 is a pair of compression clips positioned on opposite sides of an upper lip 106 of the lateral pad holder 24 circumscribing the upper opening 104. Alternatively, the upper pad assembly fastener 102 can be a conventional rivet (not shown) simultaneously engaging the end 98 and upper lip 106 to retain the upper adjustment member 74 within the upper opening 104 in the manner recited above.

The lower adjustment member 88 is a conventional screw similarly positioned in the central bore 86 of the lower hinge fastener 82 such that the external threads of the lower adjustment member 88 are telescopically coupled with the internal threads of the central bore 86. The head 108 of the lower adjustment member 88 is likewise configured to receive the adjusting tool. The opposite end 110 of the lower adjustment member 88 is configured with slots 112 to receive a lower pad assembly fastener 114. The lateral pad holder 24 is provided with a lower opening 116 to receive the end 110 of the lower adjustment member 88 and about which the lower pad assembly fastener 114 is mounted, enabling fixed retention of the end 110 of the lower adjustment member 88 within the lower opening 116 of the lateral pad holder 24. The lower fastener 114 is typically substantially identical to the upper pad assembly fastener 102, enabling the lower adjustment member 88 to rotate freely relative to the lower pad assembly fastener 114 and the lateral pad holder 24 without permitting substantial linear longitudinal movement of the lower adjustment member 88 within the lower opening 116.

Operation of the adjustable lateral hinge assembly 14 is illustrated with reference to FIGS. 4–6. FIG. 4 shows the lateral hinge assembly 14 in a fully retracted position, wherein the upper and lower adjustment members 74, 88 are both in a retracted position within the central bores 72, 86, respectively, such that the heads 96, 108 are substantially flush with the tops of the upper and lower hinge fasteners 68, 82, respectively. The lateral pad holder 24 is proximate the inner hinge plate 60 when the lateral hinge assembly 14 is in the retracted position. Accordingly, when the orthopedic knee brace 10 is mounted on the leg with the lateral hinge assembly 14 in the retracted position, the degree of normal lateral force applied to the knee joint by the orthopedic knee brace 10 via the lateral pad 26 is minimized.

Figure 5:
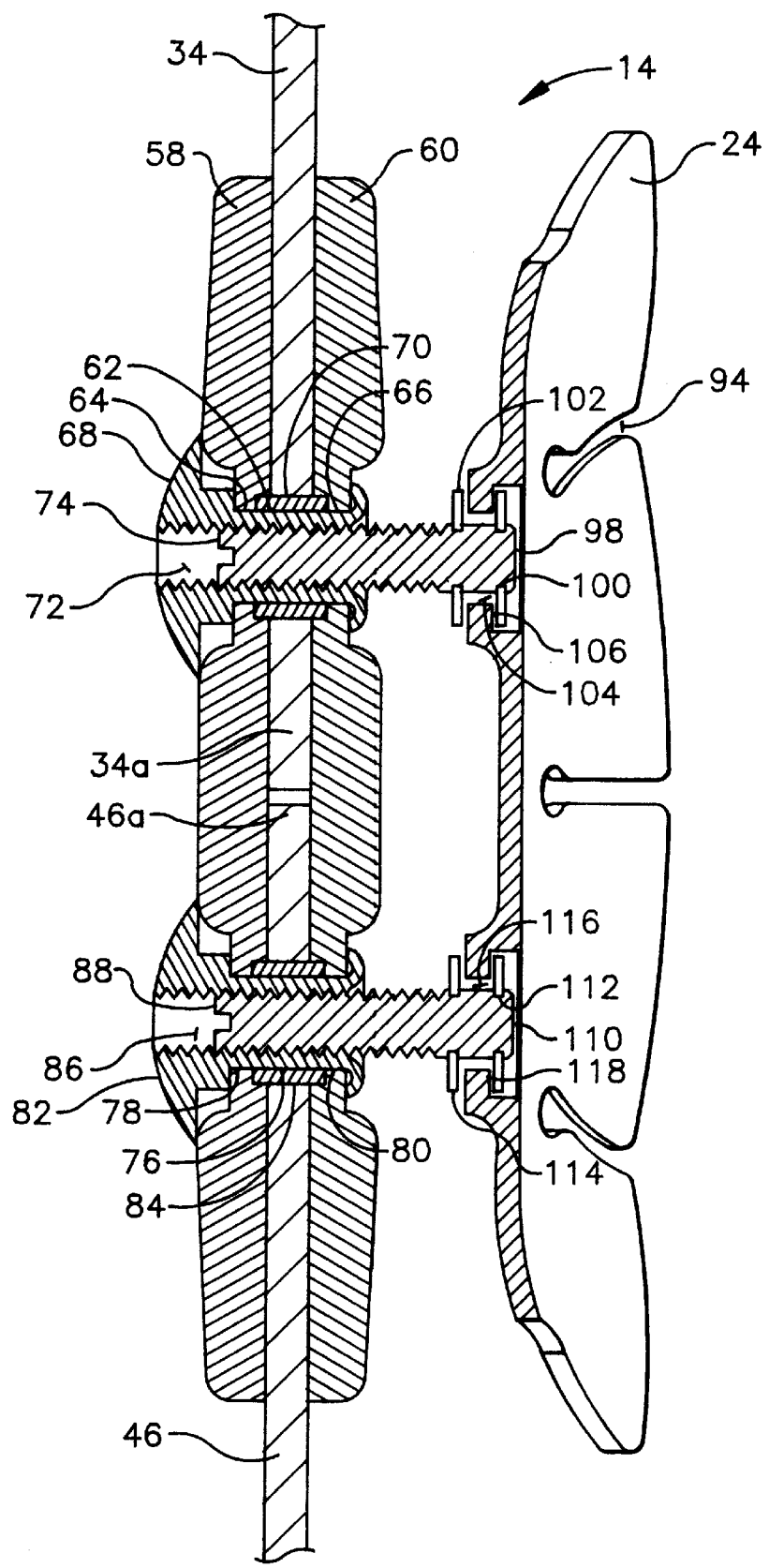
FIG. 5 is a cross-sectional view of the adjustable hinge assembly of FIG. 1 shown in a balanced extended position.

FIG. 5 shows the lateral hinge assembly 14 in a balanced extended position, wherein the upper and lower adjustment members 74, 88 are both in an extended position within the central bores 72, 86, respectively, such that both heads 96, 108 are depressed substantially the same distance below the tops of the upper and lower hinge fasteners 68, 82, respectively. The balanced extended position is achieved by turning the upper and lower adjustment members 74, 88 within the central bores 72, 86 using an adjusting tool until the entire lateral pad holder 24 is displaced a desired uniform distance away from the inner hinge plate 60. Accordingly, when the orthopedic knee brace 10 is mounted on the leg with the lateral hinge assembly 14 in the balanced extended position, the degree of normal lateral force applied to the knee joint by the orthopedic knee brace 10 across the entire lateral pad 26 is increased. As a result, the balanced extended position of the lateral hinge assembly 14 desirably mitigates the deleterious effects of osteoarthritis.

Figure 6:
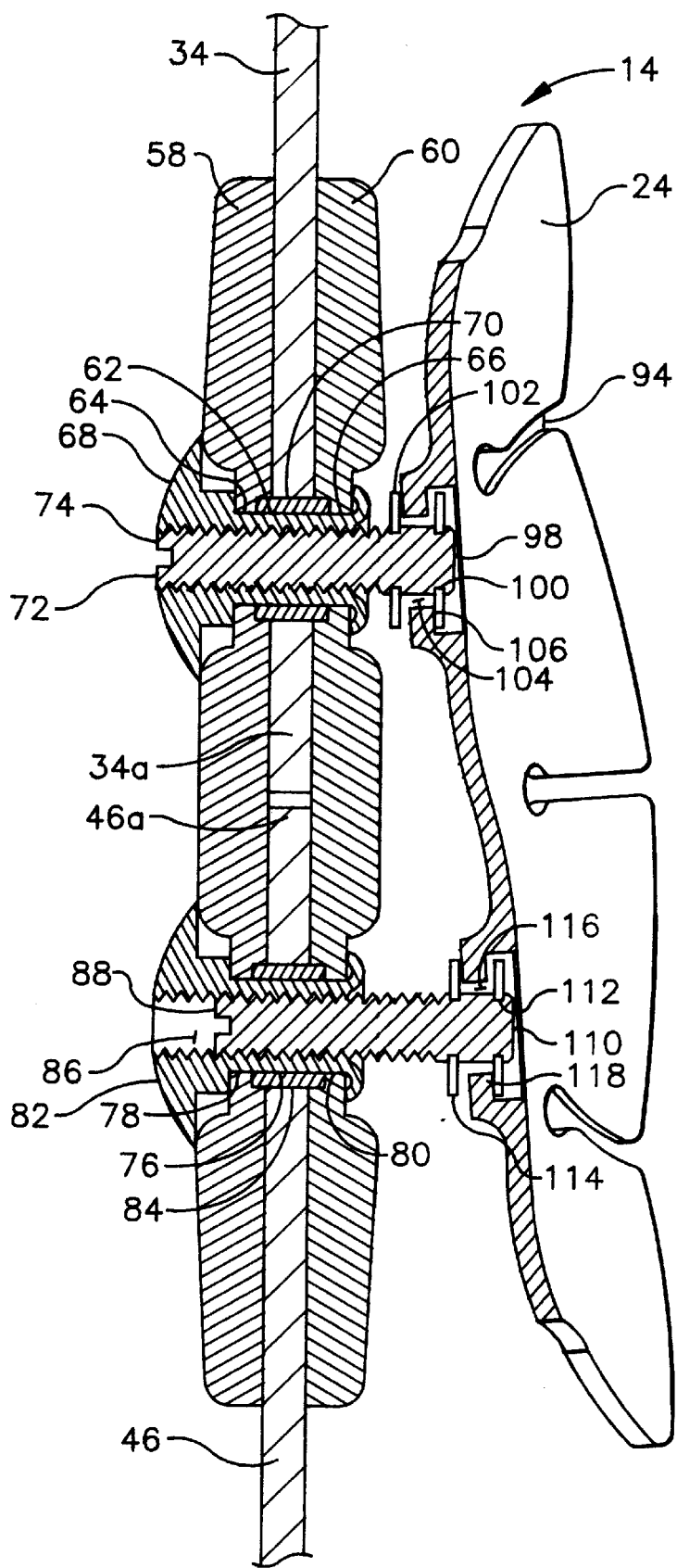
FIG. 6 is a cross-sectional view of the adjustable hinge assembly of FIG. 1 shown in an unbalanced extended position.

FIG. 6 shows the lateral hinge assembly 14 in an alternate extended position termed an unbalanced extended position, wherein only the lower adjustment member 88 is in the extended position within the central bore 86, while the upper adjustment member 74 is retained in the retracted position within the central bore 72. The unbalanced extended position is achieved by turning only the lower adjustment member 88 within the central bore 86 using the adjusting tool until the lower portion of the lateral pad holder 24 is displaced a desired distance away from the inner hinge plate 60 while the upper portion of the lateral pad holder 24 is maintained proximate the inner hinge plate 60. Accordingly, when the orthopedic knee brace 10 is mounted on the leg with the lateral hinge assembly 14 in the unbalanced extended position, an increased, but unbalanced, substantially normal lateral force is applied to the knee joint by the orthopedic knee brace 10 across the lower portion of the lateral pad 26. As a result, the unbalanced extended position of the lateral hinge assembly 14 provides an alternate position for desirably mitigating the deleterious effects of osteoarthritis.

Although not shown, it is readily apparent to the skilled artisan that an alternate unbalanced extended position is within the scope of the present invention, wherein only the upper adjustment member 74 is in the extended position within the central bore 72, while the lower adjustment member 88 is retained in the retracted position within the central bore 86. This unbalanced extended position is achieved by turning only the upper adjustment member 74 within the central bore 72 using the adjusting tool until the upper portion of the lateral pad holder 24 is displaced a desired distance away from the inner hinge plate 60 while the lower portion of the lateral pad holder 24 is maintained proximate the inner hinge plate 60. Accordingly, when the orthopedic knee brace 10 is mounted on the leg with the lateral hinge assembly 14 in the unbalanced extended position, an increased, but unbalanced, substantially normal lateral force is applied to the knee joint by the orthopedic knee brace 10 across the upper portion of the lateral pad 26.

It is further apparent that the degree of the normal lateral force applied to the knee joint by the orthopedic knee brace 10 in accordance with the present invention is fully adjustable across an entire range of balanced or unbalanced lateral forces as a function of the degree of extension the user selects and provides the upper and/or lower adjustment member 74, 88 within the central bores 72, 86, respectively.

As noted above, the orthopedic knee brace 10 disclosed herein is exemplary of orthopedic braces having utility with the adjustable hinge assembly of the present invention. It is specifically noted that the medial hinge assembly 12 of the orthopedic knee brace 10 is not adjustable in the manner of the lateral hinge assembly 14. Thus, the medial hinge assembly 12 lacks the above-described adjustment means with respect to the lateral hinge assembly 14. The non-adjustable medial hinge assembly 14 having utility with the orthopedic knee brace 10 is preferably as described in U.S. patent application 08/656,088. It is nevertheless understood that the present invention is not limited to a specific orthopedic knee brace configuration. Accordingly, it is within the scope of the present invention to provide an orthopedic knee brace having the adjustable hinge assembly of the present invention positioned both medially and laterally on the brace or positioned only medially on the brace, rather than only laterally on the brace as described herein. It is further within the scope of the present invention to provide an orthopedic knee brace having only a single adjustable hinge assembly positioned on one side of the brace, either medially or laterally, and omitting the hinge assembly and upper and lower arms from the opposing side of the brace.

While the foregoing preferred embodiments of the invention have been described and shown, it is understood that all alternatives and modifications, such as those suggested and others, may be made thereto and fall within the scope of the invention.

We claim:

1. A hinge assembly for an orthopedic knee brace comprising:
    a pad assembly configured to receive a knee joint;
    a hinge including;
        an end of a rotation member;
        a hinge plate; and
        a hinge fastener rotatably connecting said end of said rotation member to said hinge plate;
    an adjustment member telescopically engaging said hinge fastener and coupled to said pad assembly in a substantially fixed linear position relative to said pad assembly; and
    means for selectively linearly displacing said adjustment member relative to said hinge fastener while said pad assembly is maintained substantially linearly fixed relative to said adjustment member.

2. A hinge assembly for an orthopedic knee brace as recited in claim 1 wherein said selective linear displacement means is a set of coupled threads associated with said hinge fastener and said adjustment member.

3. A hinge assembly for an orthopedic knee brace as recited in claim 2 wherein said set of coupled threads is internal threads in a bore through said hinge fastener and external threads on said adjustment member received by said internal threads.

4. A hinge assembly for an orthopedic knee brace as recited in claim 1 wherein said pad assembly includes a pad holder formed from a relatively stiffened material coupled to said adjustment member and a pad formed from a cushioning material coupled to said pad holder.

5. A hinge assembly for an orthopedic knee brace as recited in claim 1 wherein said hinge plate is a first hinge plate positioned on one side of said end of said rotation member, said hinge further including a second hinge plate positioned on an opposite side of said end of said rotation member.

6. A hinge assembly for an orthopedic knee brace as recited in claim 1 further comprising a pad assembly fastener coupling said adjustment member to said pad assembly in said substantially fixed linear position relative to said pad assembly while said adjustment member is freely rotatable relative to said pad assembly.

7. A hinge assembly for an orthopedic knee brace as recited in claim 6 wherein said pad assembly fastener includes at least one compression clip engaging said adjustment member and said pad assembly.

8. A hinge assembly for an orthopedic knee brace comprising:
    a pad assembly configured to receive a knee joint;
    a hinge including;
        an end of a first rotation member;
        an end of a second rotation member;
        a hinge plate;
        a first hinge fastener rotatably connecting said end of said first rotation member to said hinge plate; and
        a second hinge fastener rotatably connecting said end of said second rotation member to said hinge plate;
    a first adjustment member telescopically engaging said first hinge fastener and coupled to said pad assembly in a substantially fixed linear position relative to said pad assembly:
    first means for selectively linearly displacing said first adjustment member relative to said hinge fastener while said pad assembly is maintained substantially linearly fixed relative to said first adjustment member;
    a second adjustment member telescopically engaging said second hinge fastener and coupled to said pad assembly in a substantially fixed linear position relative to said pad assembly; and
    second means for selectively linearly displacing said second adjustment member relative to said hinge fastener while said pad assembly is maintained substantially linearly fixed relative to said second adjustment member.

9. A hinge assembly for an orthopedic knee brace as recited in claim 8 wherein said first selective linear displacement means is a first set of coupled threads associated with said first hinge fastener and said first adjustment member and said second selective linear displacement means is a second set of coupled threads associated with said second hinge fastener and said second adjustment member.

10. A hinge assembly for an orthopedic knee brace as recited in claim 9 wherein said first set of coupled threads is first internal threads in a bore through said first hinge fastener and first external threads on said first adjustment member received by said first internal threads and said second set of coupled threads is second internal threads in a bore through said second hinge fastener and second external threads on said second adjustment member received by said second internal threads.

11. A hinge assembly for an orthopedic knee brace as recited in claim 8 wherein said pad assembly includes a pad holder formed from a relatively stiffened material coupled to said first and second adjustment members and a pad formed from a cushioning material coupled to said pad holder.

12. A hinge assembly for an orthopedic knee brace as recited in claim 8 wherein said hinge plate is a first hinge plate positioned on one side of said ends of said first and second rotation members, said hinge further including a second hinge plate positioned on an opposite side of said ends of said first and second rotation members.

13. A hinge assembly for an orthopedic knee brace as recited in claim 8 further comprising a first pad assembly fastener coupling said first adjustment member to said pad assembly in said substantially fixed linear position relative to said pad assembly while said first adjustment member is freely rotatable relative to said pad assembly and a second pad assembly fastener coupling said second adjustment member to said pad assembly in said substantially fixed linear position relative to said pad assembly while said second adjustment member is freely rotatable relative to said pad assembly.

14. A hinge assembly for an orthopedic knee brace as recited in claim 13 wherein said first pad assembly fastener includes at least one compression clip engaging said first adjustment member and said pad assembly and said second pad assembly fastener includes at least one compression clip engaging said second adjustment member and said pad assembly.

15. A hinge assembly for an orthopedic knee brace comprising:
 a pad assembly configured to receive a knee joint;
 a hinge including;
  an end of a first rotation member having a first rotation aperture;
  an end of a second rotation member having a second rotation aperture;
  a hinge plate having a first hinge aperture and a second hinge aperture;
  a first hinge fastener received within said first rotation aperture and said first hinge aperture to rotatably connect said end of said first rotation member to said hinge plate, wherein said first hinge fastener has a first bore with first internal threads; and
  a second hinge fastener received within said second rotation aperture and said second hinge aperture to rotatably connect said end of said second rotation member to said hinge plate, wherein said second hinge fastener has a second bore with second internal threads;
 a first adjustment member having first external threads received by said first internal threads to selectively linearly displace said first adjustment member relative to said first hinge fastener, while said first adjustment member is coupled to said pad assembly in a substantially fixed linear position relative to said pad assembly; and
 a second adjustment member having second external threads received by said second internal threads to selectively linearly displace said second adjustment member relative to said second hinge fastener, while said second adjustment member is coupled to said pad assembly in a substantially fixed linear position relative to said pad assembly.

16. A hinge assembly for an orthopedic knee brace as recited in claim 15 wherein said pad assembly includes a pad holder formed from a relatively stiffened material coupled to said first and second adjustment members and a pad formed from a cushioning material coupled to said pad holder.

17. A hinge assembly for an orthopedic knee brace as recited in claim 15 wherein said hinge plate is a first hinge plate positioned on one side of said ends of said first and second rotation members, said hinge further including a second hinge plate positioned on an opposite side of said ends of said first and second rotation members, further wherein said second hinge plate has a first hinge aperture and a second hinge aperture and said first hinge fastener is received within said first hinge aperture of said second hinge plate to rotatably connect said end of said first rotation member to said second hinge plate and said second hinge fastener is received within said second hinge aperture of said second hinge plate to rotatably connect said end of said second rotation member to said second hinge plate.

18. A hinge assembly for an orthopedic knee brace as recited in claim 15 further comprising a first pad assembly fastener coupling said first adjustment member to said pad assembly in said substantially fixed linear position relative to said pad assembly while said first adjustment member is freely rotatable relative to said pad assembly and a second pad assembly fastener coupling said second adjustment member to said pad assembly in said substantially fixed linear position relative to said pad assembly while said second adjustment member is freely rotatable relative to said pad assembly.

19. A hinge assembly for an orthopedic knee brace as recited in claim 18 wherein said first pad assembly fastener includes at least one compression clip engaging said first adjustment member and said pad assembly and said second pad assembly fastener includes at least one compression clip engaging said second adjustment member and said pad assembly.

* * * * *